United States Patent
Vollmüller et al.

(10) Patent No.: US 6,420,597 B2
(45) Date of Patent: Jul. 16, 2002

(54) PROCESS FOR PREPARING HIGHLY PURE FORMYLPHENYLBORONIC ACIDS

(75) Inventors: Frank Vollmüller, Frankfurt am Main; Andreas Meudt, Flörsheim-Weilbach; Stefan Scherer, Büttelborn, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/897,566

(22) Filed: Jul. 2, 2001

(30) Foreign Application Priority Data

Jul. 1, 2000 (DE) .......................... 100 32 017

(51) Int. Cl.$^7$ ................................. C07F 5/02
(52) U.S. Cl. ........................................... 562/7
(58) Field of Search ............................... 562/7

(56) References Cited

U.S. PATENT DOCUMENTS 3,714,206 A * 1/1973 Huemer et al.
5,157,149 A * 10/1992 Samsel .......................... 562/7

OTHER PUBLICATIONS

CA:113:132257 ab Chem Ber 123(9) pp. 1841–3 1990.*
Aldrich Chemical Catalogue p. 743 1996.*
Feulner, et al., Contributions to the Chemistry of Boron, 206^1)—preparation and Structural Characterization of p–Formylbenzeneboronic Acid, Chem. Ber. 123 (1990) pp. 1841–1843.
Ki Chul Park, et al., "A High Yeild Synthesis of 4–Boron-o–DL–phenylalanine", Synthesis 1990, No. 12, pp. 2041–2044.
Heiner Jendralla, et al., "Efficient Simple Procedures for Large–Scale Preparations of Building Blocks for Angiotensin (II) Receptor Antagonists", Liebigs Ann, 1995, pp. 1253–1257.
Yuichi Kobayashi, et al., "Preparation of Functionalized Zinc Borates and their Coupling Reaction with Allylic Acetates", Tetrahedron Letter, 39, (1988) pp. 7537–7540.

* cited by examiner

*Primary Examiner*—Jean F. Vollano
(74) *Attorney, Agent, or Firm*—Scott E. Hanf

(57) ABSTRACT

A process for purifying formylphenylboronic acids of the formula (I)

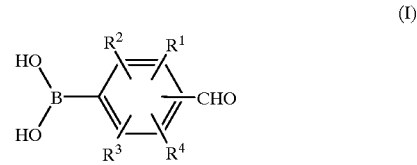

where the formyl function is located in the ortho, meta or para position relative to the boronic acid function, by dissolving the crude formylphenylboronic acids in an alkaline solvent having a pH in the range from 8 to 11 separating off the insoluble organic impurities and subsequently acidifying the alkaline boronic acid solution and separating off and working up the precipitated boronic acid. The crude formylphenylboronic acid is preferably dissolved in aqueous alkali metal or alkaline earth metal oxide, hydroxide, carbonate or phosphate solutions at temperatures in the range from 5 to 50° C. The formylphenylboronic acids obtained have a purity of ≧99% and are suitable as precursors for liquid-crystalline compounds, as liquid crystals or as constituents of liquid-crystalline mixtures or as pharmaceutical intermediates.

8 Claims, No Drawings

PROCESS FOR PREPARING HIGHLY PURE FORMYLPHENYLBORONIC ACIDS

BACKGROUND OF THE INVENTION

Formylphenylboronic acid and its substituted derivatives are customarily synthesized from the corresponding haloaromatic either as described in Liebigs Ann. 1995, 1253–1257 and Chem. Ber. 123 (1990) 1841–1843 in a yield of 94% or 78% by reaction of the corresponding protective bromoaromatic with magnesium in a Grignard reaction and subsequent addition of trialkyl borate or as described in Tetrahedron Lett 1998, 39, 7537–7540, in a yield of 99% by reaction of the corresponding protected bromoaromatic with butyllithium at −78° C. and subsequent reaction with triisopropyl borate to form the corresponding formylphenylboronic acid.

However, for the industrial preparation it is disadvantageous that a high purity can be achieved only at very low (−78° C.) and thus uneconomical temperatures and with the use of expensive organolithium compounds.

Higher temperatures both in the preparation of the organometallic compound (reflux temperature of THF in the Grignard step) and also temperatures of >−40° C. in the addition of the trialkylboric ester onto the organometallic compound frequently result in a product of unsatisfactory purity. The most frequent organic impurities are the corresponding triarylboranes and borinic acids or benzaldehyde and the correspondingly substituted hydroxybenzaldehydes and bisformylbiphenyls which can be formed during the Grignard reaction.

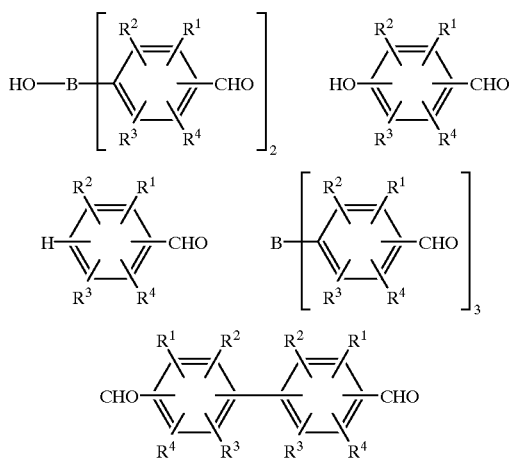

The impurities interfere when the product is used as precursor for liquid-crystalline compounds, as liquid crystals or as constituent of liquid-crystalline mixtures, in particular when the product is used as pharmaceutical intermediate or generally in applications which require very high purity.

Boronic acids are usually isolated from the reaction mixture by hydrolyzing the suspension from the borate addition and, after phase separation, distilling tetrahydrofuran (THF) from the homogeneous organic phase. During the distillation, the boronic acid precipitates from the solution and can be separated off by filtration.

The organic impurities can be separated off only incompletely, if at all, by this method.

It is possible to remove the above-described impurities by means of multiple extraction with toluene and to recrystallize the boronic acid as described in Chem. Ber. 123 (1990) 1841–1843, with great losses of yield from water or from hydrochloric acid (Synthesis 1999, 2041–2044).

Furthermore, Liebigs Ann. 1995, 1253–1257, describes the purification of 4-formylphenylboronic acid by dissolution in aqueous potassium hydroxide at pH 14, extraction of the aqueous solution with methyl t-butyl ether (MTBE) and subsequent precipitation of the boronic acid by means of sulfuric acid. Contamination visible in the NMR of 5–7% is described in the publication. Our own experiments on this showed that, for example, 4-formylphenylboronic acid reacts to a considerable extent in a Cannizzaro reaction in aqueous alkaline medium above a pH of >11. The 4-carboxyphenylboronic acid and 4-(hydroxymethyl)-phenylboronic acid formed can be separated from the mixture only with great difficulty.

SUMMARY OF THE INVENTION

It is an object of the invention to provide a process for purifying formylphenylboronic acid and its derivatives which allows the formylphenylboronic acid to be prepared in high purity and does not have the disadvantages described.

DESCRIPTION OF THE PREFERRED EMBODIMENTS

According to the present invention, this object is achieved by a process for purifying formylphenylboronic acids of the formula (I)

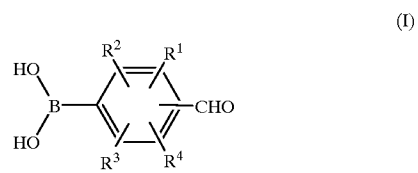

(I)

where the formyl function is located in the ortho, meta or para position, preferably in the para position, relative to the boronic acid function and $R^1$ to $R^4$ are each, independently of one another, hydrogen, $C_1$–$C_{12}$-alkyl, $C_2$–$C_{12}$-alkenyl, $C_2$–$C_{12}$-alkynyl, $C_3$–$C_{12}$-cycloalkyl, $C_1$–$C_{12}$-alkoxy, O-phenyl, O-benzyl, aryl, heteroaryl, fluorine, N(alkyl)$_2$, N[Si($C_1$–$C_4$-alkyl)$_3$]$_2$ or $CF_3$, or $R^1$ and $R^2$, and/or $R^3$ and $R^4$, together form an aliphatic or aromatic ring, by dissolving the crude formylphenylboronic acids in an alkaline solvent having a pH in the range from 8 to 11, preferably a pH in the range from 9 to 11, separating off the insoluble organic impurities and subsequently acidifying the alkaline boronic acid solution and separating off and working up the precipitated boronic acid.

In formula (I), it is preferred that $R^1$ to $R^4$ are each hydrogen, $C_1$–$C_6$-alkyl, $C_2$–$C_6$-alkenyl, $C_1$–$C_4$-alkoxy, O-phenyl, O-benzyl, aryl, heteroaryl, fluorine, N($C_1$–$C_4$-alkyl)$_2$, or $CF_3$, or $R^1$ and $R^2$, and/or $R^3$ and $R^4$, together form a saturated or unsaturated ring having not more than five or six ring atoms.

Particularly preferably, $R^1$ to $R^4$ are each hydrogen, $C_1$–$C_4$-alkyl, $C_2$–$C_4$-alkenyl, $C_1$–$C_4$-alkoxy, aryl, fluorine, N($C_1$–$C_4$-alkyl)$_2$ or $CF_3$, or $R^1$ and $R^2$, and/or $R^3$ and $R^4$, together form a fused-on cyclohexyl structure, cyclopentyl structure or together with the aromatic ring a naphthyl structure.

In the present process, the isolated crude formylphenylboronic acids are dissolved in an alkaline solvent such as aqueous solutions of alkali metal or alkaline earth metal oxides, hydroxides, carbonates or phosphates. Preference is given to using sodium hydroxide and potassium hydroxide solutions.

In the dissolution, it has to be ensured that the pH is in a range from 8 to 11, preferably from 9 to 11, particularly preferably from 9.5 to 10.5. At pH values of >11, Cannizzaro products are formed, as described above.

The organic impurities which are insoluble in the aqueous solutions used can subsequently be removed by adsorption on activated carbon or extraction with inert, water-immiscible organic solvents, for example aliphatic hydrocarbons such as various heptanes, octanes, cyclic aliphatic hydrocarbons such as cyclohexane, methylcyclohexane, aromatic hydrocarbons such as toluene, o-, m-, p-xylenes, chlorobenzene, o-, m-, p-dichlorobenzene or ethers such as diethyl ether, diisopropyl ether, dibutyl ether, methyl tert-butyl ether or methyl ethyl ketone or methyl isobutyl ketone, to name only a few.

Preference is given to using toluene, xylene or xylene derivatives, methyl tert-butyl ether.

After the impurities have been separated off, the boronic acid is precipitated again in highly pure form by acidification of the alkaline boronic acid solution. As inorganic mineral acids, preference is given to using sulfuric acid, hydrochloric acid, nitric acid or phosphoric acid. Organic acids which can be used are, for example, formic acid or acetic acid.

Preference is given to using hydrochloric acid or sulfuric acid for acidification. Filtration, washing and drying gives the highly pure arylboronic acid.

The purification, i.e. the alkaline dissolution procedure, is carried out at temperatures of from 5 to 50° C., preferably from 5 to 25° C., particularly preferably from 5 to 10° C. Purification at higher temperatures leads to decomposition products of the formyl function, e.g. in the form of a Cannizzaro reaction to give the corresponding carboxy and hydroxymethyl function. To avoid decomposition of the formylphenylboronic acids, they are thus, according to the invention, dissolved at a pH in the range from 8 to 11. This can be achieved, for example, by suspending the crude boronic acid in water and subsequently adjusting the pH of the solution to a value in the range from 8 to 11 by means of an aqueous base solution or the base itself.

The process of the invention makes it possible to prepare arylboronic acids having a purity of ≧99%, in particular ≧99.5%, in a suitable and economical manner. The arylboronic acids obtained in this way are very useful as precursors for liquid-crystalline compounds, as constituents of liquid-crystalline mixtures or as pharmaceutical intermediates.

EXAMPLES

Example 1: 4-Formylphenylboronic Acid 385 g of crude 4-formylphenylboronic acid (purity according to HPLC: 95%) are suspended in 2 l of water and cooled to 10° C. 1025 ml of 10% strength aqueous sodium hydroxide are added dropwise over a period of 3.5 hours at such a rate that the internal temperature does not exceed 10° C. and the pH does not exceed 10.5. After the mixture has been stirred for another 30 minutes, the precipitate is filtered off, the aqueous phase is then extracted twice with 250 ml each time of toluene. The boronic acid is subsequently precipitated again at an internal temperature of 10° C. by means of 230 ml of concentrated hydrochloric acid. The precipitate is filtered off, washed with water and dried at 50° C. in a stream of nitrogen. This gives 345 g of 4-formylphenylboronic acid (94% of theory) as a pale yellow solid having a purity of 99.6% (HPLC).

Example 2: 4-Formylphenylboronic Acid

The procedure of Example 1 is repeated using adsorption on 25 g of activated carbon, giving 4-formylphenylboronic acid having a purity of 99.4%.

Example 3: 3-Formylphenylboronic Acid 250 g of crude 3-formylphenylboronic acid (purity according to HPLC: 96%) are suspended in 1300 ml of water and cooled to 10° C. 670 ml of 10% strength aqueous sodium hydroxide are added dropwise over a period of 2.5 hours at such a rate that the internal temperature does not exceed 10° C. and the pH does not exceed 10.5. After the mixture has been stirred for another 30 minutes, the precipitate is filtered off, the aqueous phase is then extracted twice with 150 ml each time of toluene. The boronic acid is subsequently precipitated again at an internal temperature of 10° C. by means of 150 ml of concentrated hydrochloric acid. The precipitate is filtered off, washed with water and dried at 50° C. in a stream of nitrogen. This gives 237.1 g of 3-formylphenylboronic acid (95% of theory) as a pale yellow solid having a purity of 99.5% (HPLC).

Example 4: 2-Formylnaphthyl-1-boronic Acid 23 g of crude 2-formylnaphthyl-1-boronic acid (purity according to HPLC: 96%) are suspended in 100 ml of water and cooled to 10° C. 48 ml of 10% strength aqueous sodium hydroxide are added dropwise over a period of 1 hour at such a rate that the internal temperature does not exceed 10° C. and the pH does not exceed 10.5. After the mixture has been stirred for another 10 minutes, the precipitate is filtered off, the aqueous phase is then extracted twice with 50 ml each time of toluene. The boronic acid is subsequently precipitated again at an internal temperature of 10° C. by means of 45 ml of 10% strength hydrochloric acid. The precipitate is filtered off, washed with water and dried at 50° C. in a stream of nitrogen. This gives 20.5 g of 2-formylnaphthyl-1-boronic acid (89% of theory) as a light-yellow solid having a purity of 99.3% (HPLC).

Example 5: 3-Fluoro-4-formylphenylboronic acid 33 g of crude 3-fluoro-4-formylphenylboronic acid (purity according to HPLC: 93%) are suspended in 250 ml of water and cooled to 10° C. 75 ml of 10% strength aqueous sodium hydroxide are added dropwise over a period of 1.5 hour at such a rate that the internal temperature does not exceed 10° C. and the pH does not exceed 10.5. After the mixture has been stirred for another 10 minutes, the precipitate is filtered off, the aqueous phase is then extracted twice with 50 ml each time of toluene. The boronic acid is subsequently precipitated again at an internal temperature of 10° C. by means of 77 ml of 10% strength hydrochloric acid. The precipitate is filtered off, washed with water and dried at 50° C. in a stream of nitrogen. This gives 29 g of 3-fluoro-4-formylphenylboronic acid (94.4% of theory) as a light-yellow solid having a purity of 99.7% (HPLC).

Example 6: 3-Formyl-4-methoxyphenylboronic Acid 25 g of crude 3-formyl-4-methoxyphenylboronic acid (purity according to HPLC: 96%) are suspended in 200 ml of water and cooled to 10° C. 58 ml of 10% strength aqueous sodium hydroxide are added dropwise over a period of 1.5 hour at such a rate that the internal temperature does not exceed 10° C. and the pH does not exceed 10.5. After the mixture has been stirred for another 10 minutes, the precipitate is filtered off, the aqueous phase is then extracted twice with 50 ml each time of toluene. The boronic acid is subsequently precipitated again at an internal temperature of 10° C. by means of 60 ml of 10% strength hydrochloric acid. The precipitate is filtered off, washed with water and dried at 50° C. in a stream of nitrogen. This gives 22.1 g of 3-formyl-4-methoxyphenylboronic acid (92% of theory) as a colorless solid having a purity of 99.6% (HPLC).

Comparative Example: 4-Formylphenylboronic Acid

Using a method based on that in Liebigs Ann. 1995, 1253–1257, a solution of 120 g of tri-n-butyl borate in 250 g of dry tetrahydrofuran was placed under nitrogen in a dried 2 l flask fitted with a dropping funnel and cooled to -50° C. 535 g of a 26.5% strength solution of 4-diethoxymethylphenylmagnesium bromide in THF are then added dropwise at such a rate that the internal temperature does not exceed −40 to −50° C. The mixture is subsequently stirred at −50° C for another 1 hour. 1 l of methyl t-butyl ether (MTBE) is subsequently added and the mixture is hydrolyzed at 5–10° C. using 650 g of 1M sulfuric acid. The aqueous phase was separated off and extracted three times with 500 ml each time of methyl t-butyl ether. The solvent was distilled off under reduced pressure and the crude boronic acid was once again taken up in 0.5 l of water and 185 ml of 5N aqueous potassium hydroxide (pH 14) at 5° C. The aqueous phase was extracted once with 250 ml of MTBE and subsequently, at 5° C., brought to a pH of 1 using 400 ml of 1M sulfuric acid. The precipitate was filtered off, washed twice with 150 ml of ice water and dried. This gives 66.1 g of 4-formylphenylboronic acid (88% of theory) comprising, according to HPLC, 89% of 4-formylphenylboronic acid, 4% of 4-carboxyphenylboronic acid, 3.8% of 4-hydroxymethylphenylboronic acid.

What is claimed is:

1. A process for purifying formylphenylboronic acids of the formula (I)

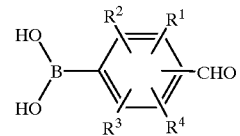

where the formyl function is located in the ortho, meta or para position relative to the boronic acid function and $R^1$ to $R^4$ are each, independently of one another, hydrogen, $C_1$–$C_{12}$-alkyl, $C_2$–$C_{12}$-alkenyl, $C_2$–$C_{12}$-alkynyl, $C_3$–$C_{12}$-cycloalkyl, $C_1$–$C_{12}$-alkoxy, O-phenyl, O-benzyl, aryl, heteroaryl, fluorine, $N(alkyl)_2$, $N[Si(C_1$–$C_4$-alkyl)_3]_2$ or $CF_3$, or $R^1$ and $R^2$, and/or $R^3$ and $R^4$, together form an aliphatic or aromatic ring, by dissolving the crude formylphenylboronic acids in an alkaline solvent having a pH in the range from 8 to 11, separating off the insoluble organic impurities and subsequently acidifying the alkaline boronic acid solution and separating off and working up the precipitated boronic acid.

2. The process as claimed in claim 1, wherein the crude formylphenylboronic acid is dissolved in aqueous alkali metal or alkaline earth metal oxide, hydroxide, carbonate or phosphate solutions.

3. The process as claimed in claim 1, wherein the purification is carried out temperatures in the range from 5 to 50° C.

4. The process as claimed in claim 1, wherein the organic impurities are removed by adsorption on activated carbon or extraction with inert, water-immiscible solvents.

5. The process as claimed in claim 1, wherein the formylphenylboronic acid obtained has a purity of ≧99%.

6. The process as claimed in claim 2, wherein the purification is carried out temperatures in the range from 5 to 50° C.

7. The process as claimed in claim 2, wherein the organic impurities are removed by adsorption on activated carbon or extraction with inert, water-immiscible solvents.

8. The process as claimed in claim 2, wherein the formylphenylboronic acid obtained has a purity of ≧99%.

* * * * *